US011033204B2

(12) United States Patent
Massonneau et al.

(10) Patent No.: US 11,033,204 B2
(45) Date of Patent: Jun. 15, 2021

(54) METHOD FOR DETERMINING AN OPHTHALMOLOGICAL PARAMETER

(71) Applicant: SURICOG, Paris (FR)

(72) Inventors: Marc Massonneau, Tillieres sur Avre (FR); Marc Swynghedauw, Paris (FR); Kristen Le Liboux, Paris (FR)

(73) Assignee: SURICOG, Paris (FR)

( * ) Notice: Subject to any disclaimer, the term of this patent is extended or adjusted under 35 U.S.C. 154(b) by 0 days.

(21) Appl. No.: 15/761,183

(22) PCT Filed: Sep. 19, 2016

(86) PCT No.: PCT/EP2016/072161
§ 371 (c)(1),
(2) Date: Mar. 19, 2018

(87) PCT Pub. No.: WO2017/046419
PCT Pub. Date: Mar. 23, 2017

(65) Prior Publication Data
US 2018/0256072 A1    Sep. 13, 2018

(30) Foreign Application Priority Data

Sep. 18, 2015    (FR) .................................... 1558825

(51) Int. Cl.
*A61B 5/107*    (2006.01)
*A61B 3/11*    (2006.01)
(Continued)

(52) U.S. Cl.
CPC .............. *A61B 5/1072* (2013.01); *A61B 3/11* (2013.01); *A61B 3/111* (2013.01); *A61B 3/113* (2013.01);
(Continued)

(58) Field of Classification Search
CPC ... A61B 5/1072; A61B 5/6815; A61B 5/6814; A61B 5/6803; A61B 5/1071;
(Continued)

(56) References Cited

U.S. PATENT DOCUMENTS 7,794,085 B2    9/2010    Bonnin
8,459,792 B2    6/2013    Wilson
(Continued)

FOREIGN PATENT DOCUMENTS

CN    1726863 A    2/2006
CN    1971608 A    5/2007
(Continued)

OTHER PUBLICATIONS

Jan. 3, 2017 International Search Report issued in International Patent Application No. PCT/EP2016/072161.
(Continued)

*Primary Examiner* — Tuyen Tra
(74) *Attorney, Agent, or Firm* — Shumaker, Loop & Kendrick, LLP

(57) ABSTRACT

The invention relates to a method for determining at least one ophthalmological parameter of a subject, consisting of the subject's semi-pupillary distances, comprising observing the subject's two eyes using an eye tracking device (30) borne by the subject and determining the aforementioned parameter at least from this observation.

22 Claims, 1 Drawing Sheet

Figure 1:
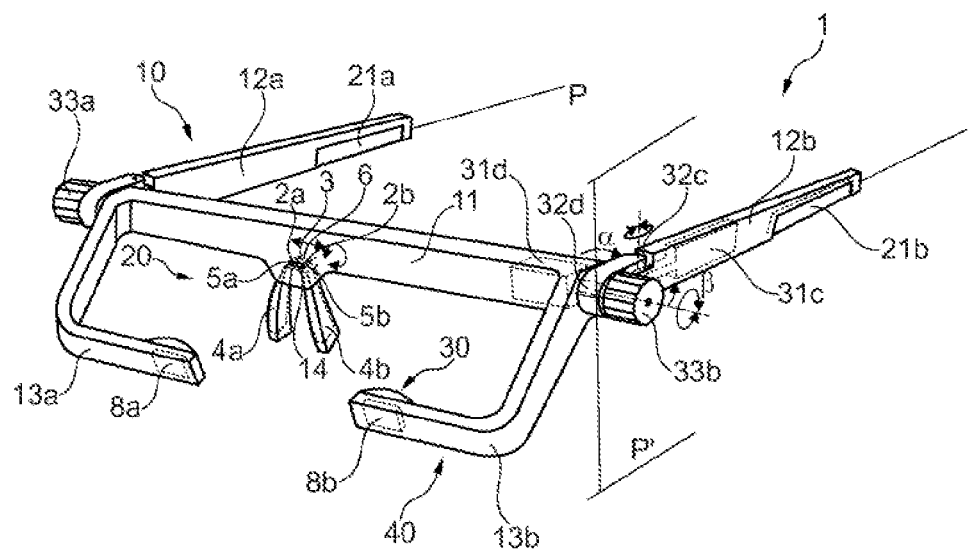

(51) Int. Cl.
*A61B 3/113* (2006.01)
*A61B 5/00* (2006.01)
*G06F 3/01* (2006.01)
*G06F 1/16* (2006.01)
*A61B 3/032* (2006.01)

(52) U.S. Cl.
CPC .......... *A61B 5/1071* (2013.01); *A61B 5/6803* (2013.01); *A61B 5/6814* (2013.01); *A61B 5/6815* (2013.01); *G06F 1/163* (2013.01); *G06F 3/013* (2013.01); *A61B 3/032* (2013.01)

(58) Field of Classification Search
CPC . A61B 3/113; A61B 3/111; A61B 3/11; A61B 3/032; G06F 1/163; G06F 3/013
USPC .................................................. 351/200, 204
See application file for complete search history.

(56) References Cited

U.S. PATENT DOCUMENTS

| | | | | |
|---|---|---|---|---|
| 9,658,453 | B1* | 5/2017 | Kress | ................. G02B 27/0172 |
| 10,217,286 | B1* | 2/2019 | Angel | ................... G06T 19/006 |
| 2003/0081173 | A1 | 5/2003 | Dreher | |
| 2006/0077558 | A1 | 4/2006 | Urakawa | |
| 2015/0042558 | A1 | 2/2015 | Massonneau | |
| 2015/0131051 | A1 | 5/2015 | Huang | |
| 2016/0178904 | A1* | 6/2016 | Deleeuw | ................. G06F 3/011 345/8 |

FOREIGN PATENT DOCUMENTS

| | | |
|---|---|---|
| CN | 101067684 A | 11/2007 |
| CN | 101238497 A | 8/2008 |
| CN | 101273880 A | 10/2008 |
| CN | 102188248 A | 9/2011 |
| CN | 103293676 A | 9/2013 |
| CN | 103748599 A | 4/2014 |
| CN | 104094280 A | 10/2014 |
| CN | 102961119 B | 1/2015 |
| EP | 2062090 B1 | 5/2009 |
| EP | 2400880 B1 | 11/2013 |
| FR | 2989482 A1 | 10/2013 |
| FR | 3011952 A1 | 4/2015 |
| WO | 2013/086137 A1 | 6/2013 |
| WO | 2014/006516 A1 | 1/2014 |
| WO | 2014/077462 A1 | 5/2014 |

OTHER PUBLICATIONS

CN Office Action for CN App. No. 201680067360.0 dated Sep. 1, 2020 (35 pages).

* cited by examiner

METHOD FOR DETERMINING AN OPHTHALMOLOGICAL PARAMETER

The present invention concerns the determination of anatomical parameters useful for the design and/or the choice of frames and/or lenses adapted to suit a subject.

It is known to measure the characteristics of the face of a subject relative to a specific design of frame chosen by the subject using a fixed terminal or a tablet. The company Essilor, with its EyeCode and M'eye Fit Touch technologies, the companies Acep, Zeiss and Visionix, and also the company Hoya, with its VisuReal+ technology, propose an approach of this kind.

The company Experoptic proposes a measuring kit including a frame to be assembled that is intended to be photographed when it is worn by the subject. The measurements and photographs are submitted via the Internet and the spectacles manufactured remotely and then delivered.

The application WO 2014/006516 A1 describes a system including an external video camera for taking a photograph in order to determine the interpupillary distance of a subject. The application WO 2013/086137 A1 teaches a method of determining the interpupillary distance of a subject by taking a photograph using a video camera placed in front of the face of the subject. The U.S. Pat. No. 8,459,792 B2 discloses a method of determining the interpupillary distance of a subject by taking a photograph after placing a reference support on their forehead.

The patent EP 2 062 090 B1 discloses a video camera connected to a computer that remotely observes a subject fitted with a frame. The application WO 2014/077462 A1 describes a method of measuring an eye rotation angle using an external video camera.

The document U.S. Pat. No. 7,794,085 B2 describes a device for determining the rotation center of an eye of a subject in particular using a distant target. The patent EP 2 400 880 B1 teaches a method of determining the eye rotation center based on the description of the surface of the cornea by a mathematical model, the surface of the cornea being observed in two different positions by a remote device.

The measurements described in the above documents are laborious and necessitate the presence of external rather than built-in devices that observe the eye of the subject from a distance.

Because they are far from the eye of the subject, these external devices also lead to some inaccuracy of the measurement.

The application US 2006/0077558 discloses a device for precisely detecting the position of the pupil. The interpupillary distance can be calculated.

US 2015/0131051 discloses another device for calculating the position of the pupil for the identification of the iris.

The application US2015/0042558 discloses a device for determining the direction of the gaze configured to calculate inter alia the position of the rotation center of the eye.

None of the above applications aims to deliver data relating to anatomical parameters with the aim of manufacturing lenses and/or frames, and in particular are not aimed at determining the interpupillary half-distances, which are most often different on the left and on the right in the same person and a knowledge of which is useful for optimum adaptation of the lenses and/or the frame to the person.

There is therefore a requirement to simplify the determination of ophthalmological parameters and to improve accuracy, in particular with the aim of selecting and/or manufacturing the lenses of a frame and/or the latter.

Method of Determining Ophthalmological Parameter(s)

According to a first of its aspect, the invention therefore consists in a method of determining one or more ophthalmological parameters of a subject, chosen from their interpupillary distance, their interpupillary half-distances, the position of the rotation center of their eyes, and the position of their pupils when their gaze is focused at infinity, including observation of both eyes of the subject by a gaze tracking device worn by the subject and determining said parameter or parameters at least from said observation.

The determination method according to the invention enables direct working in the context of the face, as close as possible to the eye, thereby improving accuracy. It does not necessitate any remote observation. It is compatible with standard data processing systems such as computers, tablets and smartphones.

Device Placed on the Subject

The gaze tracking device can be worn by the subject by way of a device placed on the subject including the gaze tracking device, the device placed on the subject being in particular a frame, a mask, a helmet or an over-frame, in particular a spectacle type frame.

The device placed on the subject can include a positioning frame of reference intended to be positioned in a predefined manner relative to the nose of the subject, in particular intended to be aligned with its median axis.

Gaze Tracking Device

The gaze tracking device can include at least one optical sensor per eye. Thus the gaze tracking device can include at least one left optical sensor and at least one right optical sensor. The left optical sensor observes the left eye of the subject. The right optical sensor observes their right eye.

The gaze tracking device can include two left optical sensors and two right optical sensors. Depth can therefore be reconstructed using a stereoscopic system.

The position of the left and right optical sensors on the device placed on the subject and/or the distance between those sensors is in particular known. The position of the left and right optical sensors relative to the positioning frame of reference is in particular known.

The optical sensors can be thermal or infrared sensors. The optical sensors can be associated with LEDs. The optical sensors can include a video camera, in particular an RGB video camera. The video cameras can be thermal cameras.

The gaze tracking device can include at least one right light for lighting the right eye of the subject and at least one left light for lighting the left eye of the subject, each light emitting in particular visible and/or infrared light, polarized or non-polarized, in particular filtered in phase or in amplitude, in particular structured or not, in particular emitting a predetermined light pattern, the right and left optical sensors being respectively sensitive to the right light and to the left light.

The gaze tracking device preferably includes an on-board, wireless system.

Gaze tracking devices suitable for the invention are disclosed for example in the applications FR 2 989 482 and FR 3 011 952.

The method of determining one or more ophthalmological parameters of the subject can include a calibration phase to determine the position of the optical sensors relative to the eyes of the subject.

There can in particular be displayed on a screen, transparent or not, one or more test patterns and/or one or more patterns intended to be seen by the subject, in particular to guide their gaze.

Ophthalmological Parameters

The determination method according to the invention in particular enables determination of the interpupillary distance of the subject and/or their interpupillary half-distances and/or the position of their pupils, in particular their height, when their gaze is focused at infinity.

The methods of determining the interpupillary distance of the subject, their interpupillary half-distances, and the position of their pupils entail observation of both eyes of the subject by the gaze tracking device worn by the subject. The gaze tracking device can enable detection of the position of the pupil on each eye. The distance between the left and right optical sensors can be known or calculated from the configuration of the device placed on the subject. The device can include an adjustable length nose bridge which can be used to determine the ophthalmological parameters when in place on the subject.

The left and right interpupillary half-distances are measured relative to the median axis of the nose of the subject. They can be identical or not.

The interpupillary half-distances can be determined thanks in particular to the position of the optical sensors relative to the positioning frame of reference. The methods of determining the interpupillary distance of the subject, their interpupillary half-distances and the position of their pupils can include a calibration phase for determining the position of the optical sensors relative to the eyes.

The determination method according to the invention can also enable determination of the position of the rotation center of the eyes of the subject.

The direction of the gaze of the subject can be deduced from the image of the eyes of the subject thanks to the optical sensors. The pupil projected onto an optical sensor produces an ellipse the characteristics of which are linked to this 3D direction. The rotation center of the eye can be determined from the intersection of all the directions obtained during a given ocular scan.

Apparatus for Determining Facial Anatomical Parameters

Means for Determining the Shape of at Least a Part of the Nose of the Subject

The invention also consists in apparatus for determining one or more facial anatomical parameters of this subject including a frame to be placed on the subject, the frame including means for determining the shape of at least one part of the nose of the subject, said determination means delivering information representative of said shape.

The means for determining the shape of at least one part of the nose in particular have a known position on the frame.

At least one of the facial anatomical parameters, notably all the facial anatomical parameters, can be chosen from the width and the local inclination of the nose of the subject when the frame is placed on the subject.

The means for determining the shape of at least one part of the nose can enable determination of the distance from the nose in their area of contact with the nose of the subject.

The means for determination of the shape of at least one part of the nose can include two pivoting fins each intended to be placed against one wing of the nose and a device for adjusting the distance between the fins.

The means for determining the shape of at least one part of the nose can include two articulations each connecting the adjustment device to one fin. The articulations can each include a pivot connection.

The means for determining the shape of at least one part of the nose can include two sensors each measuring the movement in rotation of one fin relative to the adjustment device. The movement in rotation of the fins relative to the device for adjusting the distance between the fins can be incremental or continuous. The sensors measuring the movement in rotation of the fins relative to the adjustment device can be rotary potentiometers that transform an angle into an electrical resistance or optical coders.

The adjustment device can include a branch of adjustable length and a sensor measuring the axial movement of the branch. The axial movement of the adjustable length branch can be incremental or continuous. The sensor measuring the axial movement of the branch can be a linear potentiometer that transforms a length into an electrical resistance.

The means for determining the shape of at least one part of the nose can include a light-emitting diode, an optical fiber espousing the shape of at least one part of the nose, and a photodiode that transforms the luminous radiation emitted by the light-emitting diode and transmitted by the optical fiber into an electrical signal related to the shape of at least one part of the nose.

Alternatively, the means for determining the shape of at least one part of the nose can include a nose bridge chosen from a set of calibrated nose bridges adapted to different nose shapes, each of the nose bridges, when integrated into the frame, delivering information specific to it.

The information delivered by the nose bridge when integrated into the frame can be binary information.

The device placed on the subject can include an electronic device enabling automatic recognition of the chosen nose bridge.

The nose bridge, when integrated into the frame, can constitute or include a positioning frame of reference as described above.

According to another variant, the means for determining said shape can include at least one deformable flexible strip delivering information representative of the deformation that it undergoes.

The flexible strip can be a "flex" type sensor transforming a deformation into electrical resistance.

The flexible strip can also be inserted in a deformable nose bridge.

At least one of the facial anatomical parameters can be the angle of the wings of the nose of the subject or the width of their nose.

The frame can include a gaze tracking device, in particular including an optical sensor. The optical sensor can have one or more of the characteristics described above.

The frame can include a gaze tracking device observing both eyes of the subject, in particular enabling determination of one or more ophthalmological parameters of the subject, chosen from their interpupillary distance, their interpupillary half-distances, the position of the rotation center of their eyes, and the position of their pupils when their gaze is focused at infinity.

The gaze tracking device can have one or more of the features described above.

Sensor Sensitive to Contact with an Ear

According to another aspect, the invention consists in apparatus for determining one or more facial anatomical parameters of a subject, in particular as defined above, including a frame to be placed on the subject, the frame including two side branches, at least one branch including at least one sensor sensitive to contact with an ear of the subject when the frame is placed on the subject, each of the two branches preferably including a sensor sensitive to contact with an ear of the subject when the frame is placed on the subject, each sensor sensitive to contact with an ear of the subject being in particular a pressure sensor.

The sensor or sensors sensitive to contact with an ear of the subject notably have a known position on the frame.

The sensor or sensors sensitive to contact with an ear of the subject can also be sensitive to contact with the cranium of the subject.

The sensor or sensors sensitive to contact with an ear of the subject can be pressure sensors the resistance of which varies as a function of the exerted pressure.

Sensor of Side Branch Angle Divergence of Subject

According to another of its aspects, the invention further consists in apparatus for determining one or more facial anatomical parameters of a subject, in particular as defined above, including a frame, the frame including two side branches and at least one side branch angle divergence sensor, in particular a side branch angle divergence sensor for each side branch.

The side branch angle divergence sensor or sensors can be rotary potentiometers that transform an angle into electrical resistance.

Alternatively, the side branch angle divergence sensor or sensors can be inclination sensors, such as for example the Capteur d'inclinaison CMS (±0.25 V) 5 V typ. 4 mA Gamme(s) de mesure±90° Murata SCA100T-D02 marketed by the company Conrad, or angle sensors, such as for example the Set avec capteur d'angle/position et aimant AS500106 180° alim 5 V/DC sortie 0.5-4.5 V Cherry Switches CU103602, marketed by the company Conrad.

The frame can include two side branch divergence sensors for one side branch. The frame can include two side branch divergence sensors for each side branch.

The frame can include a front branch and the side branch divergence sensor or sensors can enable determination of the position of one or both side branches relative to the front branch.

The frame can include a first pivot connection enabling movement of a side branch in a substantially horizontal first plane when the frame is worn by the subject. The first plane can in particular include the front branch. A first side branch sensor can measure the angle formed between the front branch and the side branch in the first plane.

The frame can include a second pivot connection enabling movement of a side branch in a substantially vertical second plane when the frame is worn by the subject. The second plane can in particular be perpendicular to the front branch. A second side branch sensor can measure the angle formed between the front branch and the side branch in the second plane.

The frame can include a first pivot connection and a first sensor for the same side branch, in particular for each side branch. The frame can include a second pivot connection and a second sensor for the same side branch, in particular for each side branch.

The frame can include fixing means for fixing the side branches to the front branch.

A utilization procedure, including in particular exercises to be effected by the subject, can accompany the apparatus, in particular with a view to calibration and/or optimum control of the apparatus.

At least one facial anatomical parameter of the subject can be the relative positon of their nose relative to one of their two ears or their two ears.

At least one of the facial anatomical parameters can be an ophthalmological parameter.

An electronic card, notably carrying processing algorithms, can transmit information linked to the anatomical parameters to a third party system via a cable or wireless connection.

Method of Measuring Facial Anatomical Parameters

The invention also consists in a method of measuring one or more facial anatomical parameters of a subject using apparatus according to the invention for determining one or more facial anatomical parameters of the subject.

The apparatus for determining one or more facial anatomical parameters is in particular positioned on the subject so as to be adapted to suit them and to enable the facial anatomical parameters to be measured.

The method of measuring one or more facial anatomical parameters of the subject can include a calibration step.

Lens(es) and/or Frame Selection and/or Manufacture Process

According to another aspect, the invention consists in a method of selecting and/or manufacturing one or more lenses and/or a frame including the determination of one or more ophthalmological parameters of a subject by the method according to the invention of determining one or more ophthalmological parameters of a subject and the selection and/or the manufacture of one or more lenses and/or a frame at least on the basis of that determination.

The invention also consists in a method for selecting and/or manufacturing one or more lenses and/or a frame, in particular as described above, including the determination of one or more facial anatomical parameters as defined above using apparatus according to the invention and the selection and/or the manufacture of one or more lenses and/or a frame at least on the basis of that determination.

The lenses can be corrective and/or solar.

The determination of the ophthalmological parameter or parameters and/or the facial anatomical parameter or parameters can therefore be used for the manufacture of frames and/or for adapting them to the subject.

By "adapting" is meant the operation of fitting the subject's prescription lenses to the frame chosen by them. It essentially consists in trimming the lens before it is fixed to the frame, so that the optical center of the lens coincides with the direction of gaze of the subject when focused at infinity.

The determination of the ophthalmological parameter or parameters and/or the facial anatomical parameters can enable personalization of the frame, for example thanks to adaptation of the inclinations of the frame plane, the branch lengths, and/or the distances from the nose bridge.

The determination of the position of the pupils of the subject when their gaze is focused at infinity in the frame of reference of a frame as described above, termed the reference frame, enables mounting on another frame, termed the final frame, chosen by the subject.

According to a first variant, the reference frame is designed to coincide with the final frame, the form factors being in particular identical and the design differences limited to finishes. Mounting can be effected directly on the basis of the measurements taken using the reference frame. This refers in particular to standardized, in particular low-cost, frames.

According to a second variant, the knowledge of the position of the reference frame on the face of the subject relative to the final frame is necessary to be able to go from the frame of reference of the reference frame to that of the final frame. Frame 3D modeling techniques and face 3D scanning techniques can enable such information to be obtained.

Thus the method according to the invention enables the production of personalized lenses and frames. It also enables standardized manufacture of lenses and frames and therefore a saving of time and a reduction of costs. Prescribing and/or supplying frames and/or lenses adapted to the subject is facilitated.

FIGURES

Figure 2:
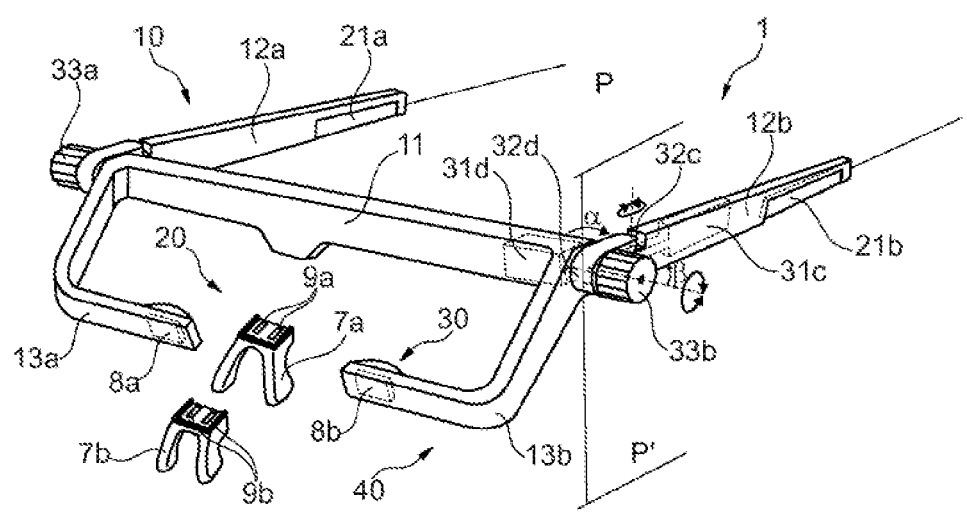

The invention will be better understood on reading the following detailed description of nonlimiting embodiments thereof and examining the drawing, in which:

FIG. 1 represents one example of apparatus according to the invention for determining one or more facial anatomical parameters, and FIG. 2 represents another example of apparatus according to the invention for determining one or more facial anatomical parameters.

The apparatus 1 for determining one or more facial anatomical parameters represented in FIG. 1 includes a device 10 in the form of a frame to be placed on a subject.

The frame 10 includes a front part 40 and two side branches 12a and 12b. The front part 40 includes a front branch 11 and two front arms 13a and 13b.

The frame 10 includes means 20 for determining the shape of at least one part of the nose of the subject delivering information representative of said shape.

The means 20 for determining the shape of at least one part of the nose of the subject include two pivoting fins 4a and 4b each intended to be placed against one wing of the nose of the subject and a device 3 for adjusting the distance between the fins.

The pivoting fins 4a and 4b are connected to the adjustment device 3 by respective pivot connections 2a and 2b.

The means 20 for determining the shape of at least one part of the nose of the subject can include two sensors 5a and 5b respectively measuring the movement in rotation of the fin 4a and of the fin 4b relative to the adjustment device 3.

The sensors 5a and 5b are for example rotary potentiometers that transform an angle into electrical resistance, such as the 3382G-1-103G three-pin resistive position sensors marketed by the company Bourns.

The means 20 for determining the shape of at least one part of the subject's nose can include a sensor 6 for measuring the axial movement of the adjustment device 3.

The sensor 6 for measuring the axial movement of the adjustment device 3 is for example a linear potentiometer that transforms a length into electrical resistance, such as the PTA4543-2015DPB103 10 k 45 mm slide potentiometer marketed by the company Bourns.

The device 3 for adjusting the distance between the fins can include a positioning marker 14 intended to be aligned with the median axis of the nose of the subject.

The means 20 for determining the shape of at least one part of the nose of the subject can enable determination of the width, the local inclination and/or the angle of the wings of the nose of the subject.

The side branches 12a and 12b include respective sensors 21a and 21b sensitive to contact with an ear of the subject when the frame is placed on the subject.

The sensors 21a and 21b sensitive to contact with an ear of the subject are for example pressure sensors such as the Force Sensitive Resistor—Small or SoftPot Membrane Potentiometer—50 mm sensors marketed by the company Sparkfun.

The frame 10 also includes two side branch angle divergence sensors 31c and 31d. These sensors 31c and 31d determine the position of the side branch 12b relative to the front part 40 of the frame 10.

The frame 10 includes a pivot connection 32c enabling movement of the side branch 12b in a plane P including the front branch 11.

The side branch angle divergence sensor 31c measures the angle α formed between the front branch 11 and the side branch 12b in the plane P including the front branch 11.

The frame 10 includes a pivot connection 32d enabling movement of the side branch 12b in a plane P' perpendicular to the front branch 11.

The side branch angle divergence sensor 31d measures the angle β formed between the front branch 11 and the side branch 12b in the plane P' perpendicular to the front branch 11.

The side branch angle divergence sensors 31c and 31d are for example rotary potentiometers that transform an angle into electrical resistance, such as the 3382G-1-103G three-pin resistive position sensors marketed by the company Bourns.

The frame 10 includes fixing means 33a and 33b for fixing the respective side branches 12a and 12b to the front part 40.

The apparatus 1 can determine the relative position of the nose and the ears of the subject thanks to the knowledge of the area of contact between the nose of the subject and the frame 10 via the means 20 for determining the shape of at least one part of the nose of the subject, the knowledge of the area of contact between the ears of the subject and the frame via the sensors 21a and 21b sensitive to contact with an ear of the subject and the knowledge of the configuration of the frame 10 via the side branch angle divergence sensors 31c and 31d.

The frame 10 also includes a gaze tracking device 30 including two optical sensors 8a and 8b, namely a right optical sensor 8a, oriented toward the right eye of the subject and a left optical sensor 8b, oriented toward their left eye.

The right optical sensor 8a and the left optical sensor 8b are respectively carried by the right front arm 13a and the left front arm 13b of the frame 10.

The gaze tracking device 30 carried by the frame 10 enables observation of both eyes of the subject.

The apparatus 1 for determining one or more facial anatomical parameters enables determination of the interpupillary distance of the subject, their interpupillary half-distances, the position of the rotation center of their eyes and/or the position of their pupils when their gaze is focused at infinity.

FIG. 2 shows a variant apparatus 1 for determining one or more facial anatomical parameters in which the means 20 for determining the shape of at least one part of the nose of the subject include a nose bridge 7a chosen from a set of calibrated nose bridges 7a and 7b adapted to different nose shapes. The subject chooses the nose bridge 7a that maximizes their comfort.

The nose bridges 7a and 7b include respective identification electronic means 9a and 9b.

The nose bridge 7a, when integrated with the frame 10, for example by clipping or clamping it on, delivers information that is specific to it thanks to the recognition of its identification means 9a by the rest of the frame 10.

Of course, the invention is not limited to the example shown and in particular features of the example shown may be combined with one another in variants that are not shown.

Other means 20 for determining the shape of at least one part of the nose of the subject are possible, for example means including a deformable flexible strip delivering information representative of the deformation to which it is subjected, such as a flex type sensor, for example the Flex Sensor 2.2" marketed by the company Sparkfun. The gaze tracking device 30 can be worn by the subject by means of a device 10 placed on the subject other than a frame, for example a mask, a helmet or an overframe. A stereoscopic system can be used to reconstruct depth, for example via a gaze tracking device 30 including two optical sensors per eye. The frame 10 can include one or more side branch angle divergence sensors for each side branch.

The invention claimed is:

1. A method of determining at least one ophthalmological parameter of a subject, the at least one ophthalmological parameter being the interpupillary half-distances, the method comprising: observing both eyes of the subject by a gaze tracking device worn by the subject and determining said parameter at least from said observation, wherein the gaze tracking device comprises at least one left optical sensor and at least one right optical sensor, the optical sensors each including a video camera, wherein:
the gaze tracking device is worn by the subject by means of a device placed on the subject including said gaze tracking device, and
the method further comprises positioning a marker of said device placed on the subject in a predefined manner relative to the nose of the subject.

2. The method as claimed in claim 1, wherein the gaze tracking device comprises two left optical sensors and two right optical sensors.

3. The method as claimed in claim 1, wherein the gaze tracking device comprises at least one right light and at least one left light, the right optical sensor(s) and left optical sensor(s) being respectively sensitive to the right light and to the left light.

4. The method as claimed in claim 1, wherein a position of a rotation center of the eyes of the subject is determined.

5. The method as claimed in claim 1, wherein a position of pupils of the subject is determined when their gaze is focused at infinity.

6. The method as claimed in claim 1, further comprising displaying on a transparent or non-transparent screen one or more test patterns and/or one or more patterns intended to be seen by the subject.

7. A method of selecting and/or manufacturing one or more lenses and/or a frame, including the determination of at least the interpupillary half-distances of a subject by the method as claimed in claim 1 and the selection and/or the manufacture of one or more lenses and/or a frame at least on the basis of that determination.

8. The method as claimed in claim 1, wherein said device placed on the subject is a frame, a mask, a helmet or an overframe.

9. An apparatus for determining one or more facial anatomical parameters of a subject including a frame to be placed on the subject, the frame including means for determining the shape of at least one part of the nose of the subject, said determination means delivering information representative of said shape.

10. The apparatus as claimed in claim 9, wherein at least one of said facial anatomical parameters is chosen from the width and the local inclination of the nose of the subject when the frame is placed on the subject.

11. The apparatus as claimed in claim 9, wherein the means for determining said shape comprises two pivoting fins that are each configured for placement against one wing of the nose and further comprises a device for adjusting the distance between the fins.

12. The apparatus as claimed in claim 9, wherein the means for determining said shape including a nose bridge is chosen from a set of calibrated nose bridges adapted to different nose shapes, each of the nose bridges, when integrated into the frame, delivering information specific to it.

13. The apparatus as claimed in claim 9, wherein the means for determining said shape comprises at least one deformable flexible strip configured for delivering information representative of the deformation to which it is subjected.

14. The apparatus as claimed in claim 9, the frame comprises a gaze tracking device observing both eyes of the subject.

15. The apparatus as claimed in claim 14, wherein the gaze tracking device enables determination of one or more ophthalmological parameters of the subject, chosen from their interpupillary distance, their interpupillary half-distances, the position of the rotation center of their eyes, and the position of their pupils when their gaze is focused at infinity.

16. The apparatus as claimed in claim 9, including a frame to be placed on the subject, the frame including two side branches, at least one branch including at least one sensor sensitive to contact with an ear of the subject when the frame is placed on the subject.

17. The apparatus as claimed in claim 9, including a frame, the frame including two side branches and at least one side branch angle divergence sensor.

18. A method of measuring one or more facial anatomical parameters of a subject using an apparatus as claimed in claim 9.

19. A method of selecting and/or manufacturing one or more lenses and/or a frame, including the determination of one or more facial anatomical parameters of a subject as claimed in claim 9 using an apparatus as claimed in claim 10 and the selection and/or the manufacture of one or more lenses and/or a frame at least on the basis of that determination.

20. A method of selecting and/or manufacturing one or more lenses and/or a frame including the determination of one or more facial anatomical parameters of a subject using an apparatus and the selection and/or the manufacture of one or more lenses and/or a frame at least on the basis of that determination, wherein:
selecting and/or manufacturing one or more lenses and/or a frame comprises a determination of at least the interpupillary half-distances of a subject by the method as claimed in claim 1 and the selection and/or the manufacture of one or more lenses and/or a frame at least on the basis of that determination; and
the determination of one or more facial anatomical parameters of the subject includes a frame to be placed on the subject, the frame including means for determining the shape of at least one part of the nose of the subject, said determination means delivering information representative of said shape.

21. A method of determining at least one ophthalmological parameter of a subject, the at least one ophthalmological parameter being the interpupillary half-distances, the method comprising: observing both eyes of the subject by a gaze tracking device worn by the subject and determining said parameter at least from said observation,
wherein the gaze tracking device comprises at least one left optical sensor and at least one right optical sensor, the optical sensors each including a video camera,
wherein a position of a rotation center of the eyes of the subject is determined and/or wherein a position of pupils of the subject is determined when their gaze is focused at infinity.

22. A method of determining at least one ophthalmological parameter of a subject, the at least one ophthalmological parameter being the interpupillary half-distances, the method comprising: observing both eyes of the subject by a gaze tracking device worn by the subject and determining said parameter at least from said observation,
    wherein the gaze tracking device comprises at least one left optical sensor and at least one right optical sensor, the optical sensors each including a video camera,
    the method further comprising displaying on a transparent or non-transparent screen one or more test patterns and/or one or more patterns intended to be seen by the subject.

* * * * *